(12) United States Patent
Nagao et al.

(10) Patent No.: US 7,576,253 B2
(45) Date of Patent: Aug. 18, 2009

(54) METHOD OF SEPARATING DIMETHYLNAPHTHALENE ISOMERS

(75) Inventors: Shinichi Nagao, Okayama (JP); Hiroshi Ogawa, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 236 days.

(21) Appl. No.: 11/722,605

(22) PCT Filed: Dec. 21, 2005

(86) PCT No.: PCT/JP2005/023482
§ 371 (c)(1),
(2), (4) Date: Jun. 22, 2007

(87) PCT Pub. No.: WO2006/068174
PCT Pub. Date: Jun. 29, 2006

(65) Prior Publication Data
US 2008/0125615 A1 May 29, 2008

(30) Foreign Application Priority Data
Dec. 24, 2004 (JP) .............................. 2004-373979

(51) Int. Cl.
*C07C 7/12* (2006.01)
(52) U.S. Cl. .................. 585/828; 585/820; 585/822
(58) Field of Classification Search ................ 585/820, 585/828, 822
See application file for complete search history.

(56) References Cited

U.S. PATENT DOCUMENTS 5,017,735 A    5/1991    Fellmann et al.
6,072,098 A * 6/2000    Takagawa et al. ........... 585/817

FOREIGN PATENT DOCUMENTS

| JP | 62-240632 | 10/1987 |
|---|---|---|
| JP | 06-065114 | 3/1994 |
| JP | 2641201 | 5/1997 |
| JP | 3157253 | 2/2001 |
| WO | WO 91/01286 | 2/1991 |

* cited by examiner

*Primary Examiner*—Tam M Nguyen
(74) *Attorney, Agent, or Firm*—Antonelli, Terry, Stout & Kraus, LLP.

(57) ABSTRACT

Use of mordenite zeolite and zeolite Y as adsorbents enables a dimethylnaphthalene isomer mixture to be efficiently separated. A feedstock oil containing a dimethylnaphthalene isomer mixture including an α,α-isomer, an α,β-isomer, and a β,β-isomer is passed through an adsorbent layer (A) including mordenite zeolite together with a developing solvent. Subsequently, a liquid discharged from the adsorbent layer (A) is passed through an adsorbent layer (B) including zeolite Y. An eluent is passed through the adsorbent layer (B). The solvent is removed from the resultant eluate to obtain the α,β-isomer of dimethylnaphthalene. Similarly, the β,β-isomer of dimethylnaphthalene is obtained from the adsorbent layer (A).

15 Claims, No Drawings

METHOD OF SEPARATING DIMETHYLNAPHTHALENE ISOMERS

TECHNICAL FIELD

The present invention relates to a method of efficiently separating a specific isomer from a feedstock oil containing a mixture of dimethylnaphthalene isomers. Naphthalenedicarboxylic acid obtained by subjecting the respective dimethylnaphthalene isomers to oxidation, or naphthalene dicarboxylic acid dimethyl ester obtained by subjecting the naphthalenedicarboxylic acid to esterification are extremely useful materials for high-performance polyester excellent in heat resistance and physical strength.

BACKGROUND ART

There are 10 kinds of isomers of dimethylnaphthalene (DMN), which are classified into three groups according to positions of 2 methyl groups on naphthalene rings: a group of $\alpha,\alpha$-isomers including 1,4-DMN, 1,5-DMN, and 1,8-DMN; a group of $\alpha,\beta$-isomers including 1,2-DMN, 1,3-DMN, 1,6-MDN, and 1,7-DMN; and a group of $\beta,\beta$-isomers including 2,3-DMN, 2,6-DMN, and 2,7-DMN. In general, purification of organic compounds is carried out by a procedure such as distillation, crystallization, and adsorption or by a combination of those. However, the DMN isomers have extremely small differences in melting point and boiling point, so it is difficult to use the simple purification method such as distillation or crystallization. For a separation method for a DMN mixture, there have been conventionally known methods and the like involving separating DMN by crystallization and by means of an adsorbent. There are known a method of separating, especially, 1,4-DMN from a DMN isomer mixture by using as an adsorbent zeolite (see, Patent Document 1), a method of selectively separating 2,6-DMN by using an auxiliary solvent for promoting adsorption and development, a desorbing agent, and zeolite Y (see, Patent Document 2), methods of separating 2,6-DMN in high purity from a feedstock oil containing 2,6-DMN, including using zeolite Y subjected to ion exchange with a cation as an absorbent and using m-xylene as a desorbing agent and a solvent (see, Patent Documents 3 and 4), and the like.

However, in those methods, selectivity of the DMN isomers is not sufficient, and the resultant DMN includes a plurality of isomers. Resins obtained from naphthalene dicarboxylic acid dimethyl ester obtained by subjecting the DMN isomer mixture to oxidation/esterification have insufficient physical and mechanical properties such as heat resistance, mechanical strength, and dimensional stability, and thus cannot be used as raw materials for polyester and the like. In particular, there have not been established a method of separating an $\alpha,\beta$-isomer from a DMN mixture containing an $\alpha,\alpha$-isomer, an $\alpha,\beta$-isomer, and a $\beta,\beta$-isomer, for example, a method of separating 1,3-DMN from a mixture of 1,3-DMN, 1,4-DMN, and 2,3-DMN. Thus, investigations have been conducted for a long period of time for attaining industrially useful separation methods by which highly pure DMN is obtained.

Patent Document 1: Japanese Patent Application Laid-Open No. 62-240632
Patent Document 2: Japanese Patent 3157253
Patent Document 3: Japanese Patent Application Laid-Open No. 6-65114
Patent Document 4: Japanese Patent 2641201

DISCLOSURE OF THE INVENTION

Problem To Be Solved By the Invention

It is an object of the present invention to solve the above-mentioned problems and to provide an industrial method, which is inexpensive and simple, of separating an $\alpha,\beta$-isomer such as 1,3-DMN from a DMN isomer mixture in high purity and high yield in a stable manner.

The inventors of the present invention have made extensive studies to solve the above-mentioned problems. The inventors of the present invention have found that an $\alpha,\beta$-isomer and a $\beta,\beta$-isomer can be separated in high purity by bringing a feedstock oil containing a DMN isomer mixture into contact with mordenite zeolite, and then with zeolite Y, and the present invention thus has been completed.

That is, according to the present invention, there is provided a method of separating a dimethylnaphthalene isomer, including: passing a feedstock oil containing a dimethylnaphthalene isomer mixture including an $\alpha,\alpha$-isomer, an $\alpha,\beta$-isomer, and a $\beta,\beta$-isomer through an adsorbent layer A including mordenite zeolite together with a developing solvent; passing a liquid which has been passed through the adsorbent layer A though an adsorbent layer B including zeolite Y; passing an eluent through the adsorbent layer B to obtain an eluate; and separating the $\alpha,\beta$-isomer from the eluate.

Further, the present invention provides a method of separating a dimethylnaphthalene isomer, including: passing a feedstock oil including a dimethylnaphthalene isomer mixture including at least a $\beta,\beta$-isomer through an adsorbent layer A including mordenite zeolite together with a developing solvent; passing an eluent through the adsorbent layer A to obtain an eluate; and separating the $\beta,\beta$-isomer of dimethylnaphthalene from the eluate.

BEST MODE FOR CARRYING OUT THE INVENTION

The feedstock oil to be used in the present invention contains a dimethylnaphthalene (DMN) isomer mixture. The DMN isomer mixture is composed of DMN isomers selected from the group consisting of: $\alpha,\alpha$-isomers including 1,4-DMN, 1,5-DMN, and 1,8-DMN; $\alpha,\beta$-isomers including 1,2-DMN, 1,3-DMN, 1,6-MDN, and 1,7-DMN; and $\beta,\beta$-isomers including 2,3-DMN, 2,6-DMN, and 2,7-DMN. The feedstock oil may contain components other than the DMN isomer mixture, but a content of the DMN isomer mixture in a feedstock oil is preferably 10% by weight or more (including 100% by weight). Examples of the components other than the DMN isomer mixture include hydrocarbons such as methylnaphthalene, ethylnaphthalene, biphenyl, alkane, cycloalkane, alkene, and cycloalkene, but the feedstock oil may contain any kinds of compounds as long as the compounds do not inhibit adsorption and separation procedures as described below. Mixing ratios of the respective DMN isomers are not particularly limited. A method of producing a feedstock oil containing the DMN isomer mixture is not particularly limited, and the feedstock oil can be obtained by, for example, isomerization of dimethylnaphthalene with a solid acid catalyst or the like, methylation of naphthalene, or disproportionation of methylnaphthalene.

For a developing solvent to be preferably used in the present invention, there is used a linear or branched aliphatic hydrocarbon or an alicyclic hydrocarbon preferably having 6 to 14 carbon atoms. Examples thereof include n-hexane, n-heptane, n-octane, isooctane, n-nonane, n-decane, n-undecane, n-dodecane, cyclohexane, decalin, and methylcyclohexane. Any one of the hydrocarbons may be used alone, or they may be mixed.

For an eluent to be preferably used in the present invention, it is preferable to use an aromatic hydrocarbon especially from a viewpoint of desorption performance. Examples thereof include benzene, toluene, o-xylene, p-xylene, m-xylene, ethylbenzene, and diethylbenzene.

The zeolite Y has a structure similar to that of natural faujasite type zeolite, and has a composition of $Na_2O.Al_2O_3.3-6SiO_2.xH_2O$. There can particularly preferably be used zeolite Y obtained by subjecting zeolite HY, zeolite NaY, or zeolite NaY to ion exchange with at least one metal ion selected from the group consisting of: alkali metals such as potassium, lithium, rubidium, and cesium; and alkaline earth metals such as barium, calcium, magnesium, strontium, and lanthanum. The zeolite Y may be used without pretreatment, or may be used after being subjected to pretreatment such as steam treatment, alkali treatment, acid treatment, or ion exchange.

The mordenite zeolite has a composition of $Na_2O.Al_2O_3.5-200SiO_2.xH_2O$. There can particularly preferably be used mordenite obtained by subjecting H mordenite, Na mordenite, or Na mordenite to ion exchange with at least one metal ion selected from the group consisting of: alkalimetals such as potassium, lithium, rubidium, and cesium; and alkali earth metals such as barium, calcium, magnesium, strontium, and lanthanum. The mordenite zeolite may be used without modification, or may be used after being subjected to pretreatment such as steam treatment, alkali treatment, acid treatment, or ion exchange.

In the present invention, first, a feedstock oil containing a DMN isomer mixture is passed through an adsorbent layer A including the mordenite zeolite together with a developing solvent, whereby the $\beta,\beta$-isomer in the feedstock oil is selectively adsorbed and developed. At this time, the feedstock oil and the developing solvent may be separately added to a separation apparatus and then may be simultaneously passed through the adsorbent layer A. Alternatively, the developing solvent may be added to the feedstock oil in advance, and then the whole maybe passed through the adsorbent layer A. An amount of the developing solvent is preferably 1 to 200 times by weight, more preferably 5 to 150 times by weight, and further more preferably 10 to 100 times by weight of an amount of DMN isomer mixture in the feedstock oil. The amount of a liquid to be passed through the adsorbent layer A is preferably within a range of 0.1 to 10 $h^{-1}$ as a supply amount (LHSV) of the feedstock oil and the developing solvent in total per unit volume of the adsorbent layer A. The adsorbent layer A has a temperature of preferably 10 to 200° C. and more preferably 20 to 150° C. when the feedstock oil and the developing oil are passed therethrough. It is preferable that a total amount of the DMN isomer mixture to be passed through the adsorbent layer A be 0.01 to 2 parts by weight with respect to 1 part by weight of the adsorbent layer A.

Next, a liquid which has been passed through the adsorbent layer A is passed through an adsorbent layer B including the zeolite Y, whereby the $\alpha,\beta$-isomer included in the passed liquid is selectively adsorbed and developed. The amount of the passed liquid to be passed through the adsorbent layer B is preferably within a range of 0.1 to 10 $h^{-1}$ as a supply amount (LHSV) of the passed liquid per unit volume of the adsorbent layer B. The adsorbent layer B has a temperature of preferably 10 to 200° C. and more preferably 20 to 150° C. when the passed liquid is passed therethrough. It is preferable that a total amount of the DMN isomer mixture to be passed through the adsorbent layer B be 0.01 to 2 parts by weight with respect to 1 part by weight of the adsorbent layer B.

Next, the eluent is passed through the adsorbent layer B to desorb the $\alpha,\beta$-isomers. The eluate discharged from the adsorbent layer B is mainly composed of the $\alpha,\beta$-isomer and the eluent solvent, and the $\alpha,\beta$-isomer can be separated by subjecting the eluent solvent to distillation or the like. The eluent solvent is preferably used in an amount of 1 to 200 times by weight of the amount of the DMN isomer mixture in the feedstock oil used in the adsorption and development. In addition, the amount of the eluent solvent to be passed through the adsorbent layer B is preferably within a range of 0.05 to 20 $h^{-1}$ as a supply amount (LHSV) of the eluent solvent per unit volume of the adsorbent layer B. The adsorbent layer B has a temperature of preferably 10 to 200° C. and more preferably 20 to 150° C. when the eluent solvent is passed therethrough.

Meanwhile, the eluent solvent can be passed through the adsorbent layer A after the adsorption and development to desorb the $\beta,\beta$-isomers. An eluate discharged from the adsorbent layer A is mainly composed of the $\beta,\beta$-isomer and the eluent solvent, and the $\beta,\beta$-isomer can be separated by subjecting the eluate to distillation or the like. The eluent solvent is preferably used in an amount of 1 to 200 times by weight of the amount of the DMN isomer mixture in the feedstock oil used in the adsorption and development. The amount of the eluent solvent to be passed through the adsorbent layer A is preferably within a range of 0.05 to 20 $h^{-1}$ as a supply amount (LHSV) of the eluent solvent per unit volume of the adsorbent layer A. The adsorbent layer A has a temperature of preferably 10 to 200° C. and more preferably 20 to 150° C. when the eluent solvent is passed therethrough.

The adsorption and separation procedures in the adsorbent layer A and/or the adsorbent layer B can be performed in various manners such as a fixed bed manner, a fluid bed manner, and a moving bed manner. However, it is preferable, from an industrial viewpoint, to perform in a simulated moving bed manner (see, for example, Japanese Patent Application Laid-Open No. 8-217700) which is an already-established technique.

EXAMPLES

Now, the present invention will be described in further detail by referring to examples. However, the present invention is not limited to these examples. Note that, in the following examples and comparative examples, feedstock oils and collected DMNs were analyzed by gas chromatography. In addition, commercially-available DMN isomers of 1,2-DMN, 1,3-DMN, 1,4-DMN, 1,5-DMN, 1,6-DMN, 1,7-DMN, 1,8-DMN, 2,3-DMN, 2,6-DMN, and 2,7-DMN (manufactured by Wako Pure Chemical Industries, Ltd.) were mixed and used.

Example 1

Commercially-available Na mordenite (manufactured by Wako Pure Chemical Industries, Ltd.) and zeolite HY (manufactured by Wako Pure Chemical Industries, Ltd.) were each loaded into a 25-ml glass tube-like column (8 mmφ×500 mm) to prepare columns containing an adsorbent layer A and an adsorbent layer B, respectively. The two columns were connected in tandem to prepare an adsorption and separation column. The adsorption and separation column was heated from outside to maintain the temperature of the respective adsorbent layers at 40° C.

Next, a feedstock oil containing a DMN isomer mixture (1,3-DMN/1,4-DMN/2,3-DMN) having a composition as shown in Table 1 was dissolved in heptane as a developing solvent to prepare a 5-wt % solution. The solution was added to the adsorption separation column, and the solution in a supply amount (LHSV) of 2.0 h$^{-1}$ was passed through the Na mordenite layer (adsorbent layer A) and the zeolite HY layer (adsorbent layer B) in the stated order for adsorption and development. The solution which had been passed through the layers had a total DMN content of 2.1 g.

After the adsorption procedure, ortho-xylene as an eluent solvent in a supply amount (LHSV) of 1.0 h$^{-1}$ was passed through the adsorbent layer B, and a solution discharged from the adsorbent layer B was collected. The collected solution was distilled to separate ortho-xylene, to thereby obtain 1,3-DMN having a purity of 98.5% in an yield of 78%.

Meanwhile, after the adsorption procedure, o-xylene as an eluent solvent in a supply amount (LHSV) of 1.0 h$^{-1}$ was passed through the adsorbent layer A, and a solution discharged from the adsorbent layer A was collected. The collected solution was distilled to separate o-xylene, to thereby obtain 2,3-DMN having a purity of 96.1% in an yield of 73%.

Example 2

The adsorption and development and the desorption from the adsorbent layer B were performed in the same manner as in Example 1 except that decane was used as the developing solvent, to thereby obtain 1,3-DMN having a purity of 88.6% in an yield of 62%.

Example 3

The adsorption and development and the desorption from the adsorbent layer B were performed in the same manner as in Example 1 except that toluene was used as the eluent solvent, to thereby obtain 1,3-DMN having a purity of 90.5% in an yield of 71%.

Comparative Example 1

The adsorption and development and the desorption from the adsorbent layer B were performed in the same manner as in Example 1 except that o-xylene was used as the developing solvent. The resultant DMNs included 59.3% of 1,3-DMN (84% yield) and the balance was other DMN isomers. Therefore, the selectivity of adsorption (separation efficiency) was extremely low.

Comparative Example 2

The adsorption and development and the desorption from the adsorbent layer B were performed in the same manner as in Example 1 except that decane was used as the eluent solvent. The resultant DMNs included 65.5% of 1,3-DMN (7% yield) and the balance was other DMN isomers. Therefore, the selectivity of adsorption (separation efficiency) was extremely low.

Comparative Example 3

The adsorption and development and the desorption from the adsorbent layer B were performed in the same manner as in Example 1 except that the adsorbent layer A was not used and that the feedstock oil was passed only through the adsorbent layer B. The resultant DMNs included 75.2% of 1,3-DMN (76% yield) and the balance was substantially 1,4-DMN. Therefore, the selectivity of adsorption (separation efficiency) was extremely low.

Comparative Example 4

The adsorption and development and the desorption from the adsorbent layer A were performed in the same manner as in Example 1 except that commercially-available sodium Y zeolite (manufactured by Wako Pure Chemical Industries, Ltd.) was used as the adsorbent for the adsorbent layer A. The resultant DMNs included 26.9% of 2,3-DMN (61% yield) and the balance was substantially 1,3-DMN. Therefore, the selectivity of adsorption (separation efficiency) was extremely low.

Comparative Example 5

The adsorption and development and the desorption from the adsorbent layer A were performed in the same manner as in Example 1 except that commercially-available 13X zeolite (manufactured by Wako Pure Chemical Industries, Ltd.) was used as the adsorbent for the adsorbent layer A. The resultant DMNs included 22.5% of 2,3-DMN (54% yield) and the balance was substantially 1,3-DMN and 1,4-DMN. Therefore, the selectivity of adsorption (separation efficiency) was extremely low.

Comparative Example 6

The adsorption and development and the desorption from the adsorbent layer A were performed in the same manner as in Example 1 except that commercially-available potassium L zeolite (manufactured by Wako Pure Chemical Industries, Ltd.) was used as the adsorbent for the adsorbent layer A. The resultant DMNs included 19.6% of 2,3-DMN (4% yield) and the balance was other DMN isomers. Therefore, both of the yield and the selectivity of adsorption (separation efficiency) were extremely low.

Example 4

The same procedures as those in Example 1 were performed except that a mixture of 1,7-DMN/2,7-DMN/1,8-DMN (see Table 2) was used as the feedstock oil. The desorption from the adsorbent layer B resulted in collection of 1,7-DMN having a purity of 89.4% in an yield of 56%. In addition, the desorption from the adsorbent layer A resulted in collection of 2,7-DMN having a purity of 90.4% in an yield of 57%.

Example 5

The same procedures as those in Example 1 were performed except that a mixture of 1,5-DMN/1,6-DMN/2,6-DMN (see Table 3) was used as the feedstock oil. The desorption from the adsorbent layer B resulted in collection of 1,6-DMN having a purity of 90.1% in an yield of 68%. In addition, the desorption from the adsorbent layer A resulted in collection of 2,6-DMN having a purity of 92.0% in an yield of 65%.

Example 6

The same procedures as those in Example 1 were performed except that a mixture of 1,2-DMN/1,4-DMN/2,3-DMN (see Table 4) was used as the feedstock oil. The desorption from the adsorbent layer B resulted in collection of 1,2-DMN having a purity of 90.1% in an yield of 68%. In addition, the desorption from the adsorbent layer A resulted in collection of 2,3-DMN having a purity of 93.8% in an yield of 61%.

INDUSTRIAL APPLICABILITY

According to the present invention, an α,β-isomer can be separated with improved selectivity from a dimethylnaphthalene isomer mixture including an α,α-isomer, the α,β-isomer, and a β,β-isomer. In addition, a β,β-isomer can be separated with improved selectivity from a dimethylnaphthalene isomer mixture including at least the β,β-isomer. According to the present invention, a specific dimethylnaphthalene isomer can be efficiently separated in high purity from a dimethylnaphthalene mixture by means of simple apparatus and procedure, and the present invention thus has large industrial significance.

TABLE 1

| DMN isomer | Classification | Composition (wt %) |
|---|---|---|
| 1,3-DMN | α,β-isomer | 56.9 |
| 1,4-DMN | α,α-isomer | 21.9 |
| 2,3-DMN | β,β-isomer | 21.2 |

TABLE 2

| DMN isomer | Classification | Composition (wt %) |
|---|---|---|
| 1,7-DMN | α,β-isomer | 58.1 |
| 2,7-DMN | β,β-isomer | 23.3 |
| 1,8-DMN | α,α-isomer | 18.6 |

TABLE 3

| DMN isomer | Classification | Composition (wt %) |
|---|---|---|
| 1,6-DMN | α,β-isomer | 53.7 |
| 1,5-DMN | α,α-isomer | 26.6 |
| 2,6-DMN | β,β-isomer | 19.7 |

TABLE 4

| DMN isomer | Classification | Composition (wt %) |
|---|---|---|
| 1,2-DMN | α,β-isomer | 54.2 |
| 1,4-DMN | α,α-isomer | 21.3 |
| 2,3-DMN | β,β-isomer | 24.5 |

The invention claimed is:

1. A method of separating a dimethylnaphthalene isomer, comprising:
    passing a feedstock oil comprising a dimethylnaphthalene isomer mixture including an α,α-isomer, an α,β-isomer, and a β,β-isomer through an adsorbent layer A including mordenite zeolite together with a developing solvent;
    passing a liquid which has been passed through the adsorbent layer A though an adsorbent layer B including zeolite Y;
    passing an eluent through the adsorbent layer B to obtain an eluate; and
    separating the α,β-isomer from the eluate.

2. A method of separating a dimethylnaphthalene isomer according to claim 1, further comprising:
    passing an eluent solvent through the adsorbent layer A to obtain an eluate after the feedstock oil and the developing solvent have been passed; and
    separating the β,β-isomer of dimethylnaphthalene from the eluate.

3. A method of separating a dimethylnaphthalene isomer according to claim 1, wherein the developing solvent comprises at least one compound selected from the group consisting of a linear aliphatic hydrocarbon, a branched aliphatic hydrocarbon, and an alicyclic hydrocarbon.

4. A method of separating a dimethylnaphthalene isomer according to claim 1, wherein the eluent comprises an aromatic hydrocarbon.

5. A method of separating a dimethylnaphthalene isomer according to claim 1, wherein an amount of the developing solvent is 1 to 200 times by weight of an amount of the dimethylnaphthalene isomer mixture in the feedstock oil.

6. A method of separating a dimethylnaphthalene isomer according to claim 1, wherein the adsorbent layer A has a temperature of 10 to 200° C. when the feedstock oil and the developing solvent are passed therethrough.

7. A method of separating a dimethylnaphthalene isomer according to claim 1, wherein the adsorbent layer B has a temperature of 10 to 200° C. when the liquid which has been passed through the adsorbent layer A and the eluent solvent are passed therethrough.

8. A method of separating a dimethylnaphthalene isomer, comprising:
    passing a feedstock oil comprising a dimethylnaphthalene isomer mixture including at least a β,β-isomer through an adsorbent layer A including mordenite zeolite together with a developing solvent;
    passing an eluent through the adsorbent layer A to obtain an eluate; and
    separating the β,β-isomer of dimethylnaphthalene from the obtained eluate.

9. A method of separating a dimethylnaphthalene isomer according to claim 8, wherein the developing solvent comprises at least one compound selected from the group consisting of a linear aliphatic hydrocarbon, a branched aliphatic hydrocarbon, and an alicyclic hydrocarbon.

10. A method of separating a dimethylnaphthalene isomer according to claim 8, wherein the eluent comprises an aromatic hydrocarbon.

11. A method of separating a dimethylnaphthalene isomer according to claim 8, wherein an amount of the developing solvent is 1 to 200 times by weight of an amount of the dimethylnaphthalene isomer mixture in the feedstock oil.

12. A method of separating a dimethylnaphthalene isomer according to claim 8, wherein the adsorbent layer A has a temperature of 10 to 200° C. when the feedstock oil and the developing solvent are passed therethrough.

13. A method of separating a dimethylnaphthalene isomer according to claim 8, wherein adsorption and separation procedures in the adsorbent layer A and/or the adsorbent layer B are performed in a simulated moving bed manner.

14. A method of separating a dimethylnaphthalene isomer according to claim 2, wherein adsorption and separation procedures in the adsorbent layer A and/or the adsorbent layer B are performed in a simulated moving bed manner.

15. A method of separating a dimethylnaphthalene isomer according to claim 1, wherein adsorption and separation procedures in the adsorbent layer A and/or the adsorbent layer B are performed in a simulated moving bed manner.

* * * * *